(12) United States Patent
Jarhede et al.

(10) Patent No.: US 9,857,364 B2
(45) Date of Patent: Jan. 2, 2018

(54) METHOD FOR DETECTION OF BINDING

(71) Applicant: GE HEALTHCARE BIO-SCIENCES AB, Uppsala (SE)

(72) Inventors: Tanja Jarhede, Uppsala (SE); Anita Larsson, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 693 days.

(21) Appl. No.: 14/359,957

(22) PCT Filed: Dec. 21, 2012

(86) PCT No.: PCT/SE2012/051469
§ 371 (c)(1),
(2) Date: May 22, 2014

(87) PCT Pub. No.: WO2013/100847
PCT Pub. Date: Jul. 4, 2013

(65) Prior Publication Data
US 2014/0322826 A1   Oct. 30, 2014

(30) Foreign Application Priority Data
Dec. 30, 2011 (SE) .................... 1151291

(51) Int. Cl.
*G01N 33/551* (2006.01)
*G01N 33/543* (2006.01)
*G01N 21/552* (2014.01)

(52) U.S. Cl.
CPC . *G01N 33/54306* (2013.01); *G01N 33/54373* (2013.01); *G01N 33/54393* (2013.01); *G01N 21/553* (2013.01)

(58) Field of Classification Search
CPC .............................. G01N 33/54373
See application file for complete search history.

(56) References Cited

U.S. PATENT DOCUMENTS 4,535,057 A * 8/1985 Dreesman ............ A61K 39/42
422/400

FOREIGN PATENT DOCUMENTS

JP   2008292270   12/2008
JP   2008292270 A * 12/2008
(Continued)

OTHER PUBLICATIONS

European Communication dated Apr. 6, 2017 (6 pages).
(Continued)

*Primary Examiner* — Chris L Chin
(74) *Attorney, Agent, or Firm* — Eversheds Sutherland (US) LLP

(57) ABSTRACT

The present invention relates to a method for detection of binding or interaction events between a binding agent and its corresponding analyte (such as an antibody and an antigen) in which a signal is detected which is substantially more amplified and thus easier to detect than in prior art systems. The method comprises simultaneous but separate addition of a first enhancement reagent having affinity for said analyte and a second enhancement reagent having affinity for the first enhancement reagent wherein the first enhancement reagent binds to the analyte and the second enhancement reagent binds to the first enhancement reagent, and, wherein the first and second enhancement reagents have more than one binding site so that they are able to bind to each other to thereby amplify a detectable signal from the binding event.

12 Claims, 5 Drawing Sheets

(56) References Cited

FOREIGN PATENT DOCUMENTS

| WO | WO 1990/011525 | 10/1990 |
|---|---|---|
| WO | WO 1992/018867 | 10/1992 |
| WO | WO 2009/070742 | 6/2009 |

OTHER PUBLICATIONS

Luo et al., "PDMS Microfluidic Devices for Optical Detection of Protein Immunoassay Using Gold Nanoparticles," Lab Chip, 2005, 5:726-729.
Hosokawa, K., et al., Analytical Chemistry, 2007, vol. 79, No. 15, pp. 6000-6004.
Supplementary European Search Report for EP Application No. 12 86 1619 dated Jan. 15, 2015 (2 pages).
Chu et al., "Quartz Crystal Microbalance Immunoassay with Dendritic Amplification Using Colloidal Gold Immunocomplex," Sensors and Actuators B, 2006, 114:696-704.
Hosokawa et al., "Ultrasensitive Immunoassay on a Power-Free Microchip with Laminar Flow-Assisted Signal Amplification," 11th International Conference on Miniaturized Systems for Chemistry and Life Sciences, Microtas 2007, XP040568554.

\* cited by examiner

METHOD FOR DETECTION OF BINDING

CROSS-REFERENCE TO RELATED APPLICATIONS

This application is a filing under 35 U.S.C. 371 of international application number PCT/SE2012/051469, filed Dec. 21, 2012, published on Jul. 4, 2013 as WO 2013/100847, which claims priority to application number 1151291-0 filed in Sweden on Dec. 30, 2011.

FIELD OF THE INVENTION

The present invention relates to a method for detection of binding or interaction events between a binding agent and its corresponding analyte (such as an antibody and an antigen) in which a signal is detected which is substantially more amplified and thus easier to detect than in prior art systems.

BACKGROUND OF THE INVENTION

There is a strong demand for higher sensitivity in SPR (surface plasmon resonance) assays e.g. in concentration analysis, host cell protein assays, measurements of protein A leakage from columns and for the detection of a wide range of molecules and biomarkers in complex biological media including immunogenicity assays. In primary antibody screening a higher sensitivity and higher throughput is needed in SPR assays. An improvement of sensitivity could allow shorter injection times and by that means higher through-put.

One commonly used approach to increase sensitivity is to sequentially inject one enhancement reagent i.e. a polyclonal antibody after the injection of analyte. This will give a limited enhancement since there is a limited number of binding sites for the enhancement molecules. Pei, Wang and Wang enhanced the response of a biotinylated enhancement reagent by injection of a strepavidin-biotinylated protein complex in a SPR-instrument. However large complexes tend to lose their binding capacity to sensor chips provided with a dextran matrix. Pei, Wang and Wang used a flat $CO_2H$ layer (C1 sensor chip) in their study with large complexes but this chip has limitations in terms of unspecific binding and sensitivity.

Instead of injecting a large complex for enhancement one could build the large complex on the surface. Laminar flow-assisted dendritic amplification is a signal amplification method for biomolecular binding events in microchannels (Hosokawa et al 2007) and JP 2008292270. However, the solution relies on presenting two combinable substances in parallel laminar flows which combines in a boundary layer in a narrowly defined detection zone. This creates high demands on the flow conditions and limits also the choices of detection device.

One could achieve a dendritic amplification by alternately inject the two enhancement molecules with ordinary injections (Yamaguchi and Harada). However repeated injections of two enhancement molecules is time consuming and also consumes considerable amounts of material.

All the above described prior art methods present significant limitations for efficient and high enhancement amplifications in flow cell assays formats, such as lengthy assays with multiple steps, high consumption of enhancement reagents, demands on delicate detection configurations as well as unspecific binding and lack of sensitivity. There is therefore a need for a quick an easy-to-perform assay that permits determination of an analyte by using an amplification step that is well suited for flow cell applications.

SUMMARY OF THE INVENTION

The present invention provides a method for detection of binding events between a binding agents and its corresponding analyte (such as an antibody and an antigen) in which a signal is detected which is substantially more amplified and thus easier to detect than in prior art systems. In this invention dendritic amplification is combined with preferably a label free detection, such as surface plasmon resonance (SPR) by mixing a solution of a pair of multivalent molecules in a fluidic system and measuring the signal immediately after the two solutions have been substantially mixed. In contrast to above described prior art, this method provides a way to break a laminar flow and obtain a more efficient mixing before the detection area and thereby allow for increased amplification efficiency and less constraints on the detection device.

In a first aspect, the invention provides a method for detection of a binding event between a binding agent in a label free detection system, for example on a solid SPR (surface plasmon resonance) surface and an analyte binding to said binding agent, comprising simultaneous but separate addition of a first enhancement reagent having affinity for said analyte and a second enhancement reagent having affinity for said first enhancement reagent, wherein the first enhancement reagent binds to the analyte and the second affinity agent binds to the first enhancement reagent, and wherein the first and second enhancement reagents have more than one binding site so that they also are able to bind to each other to thereby amplify a detectable signal from the binding event.

The binding agent and the enhancement reagents may be selected from the group consisting of antibodies, antigen binding fragments thereof, protein A and fragments and variants thereof (including SuRe ligand), protein G and fragments and variants thereof, protein L and fragments and variants thereof, or proteins with multiple tags, or avidine or streptavidine, or bivalent or multivalent molecules of other types, or poly nucleic acids.

One of the enhancement molecules recognize the bound molecule (analyte) that shall be detected. The other enhancement molecule recognizes the first enhancement molecule. Enhancement molecules that are multivalent, e.g. polyclonal antibodies, have the capacity to form large dendritic complexes.

The analysed sample may for example be a complex biological fluid, such as serum or a cell extract. The method of the invention is very sensitive and can detect analytes present in trace amounts. In the examples shown below 1.56 ng/ml of the analyte beta-2-microglobulin was tested the method may detect lower amounts than this.

DETAILED DESCRIPTION OF THE INVENTION

Figure 1:
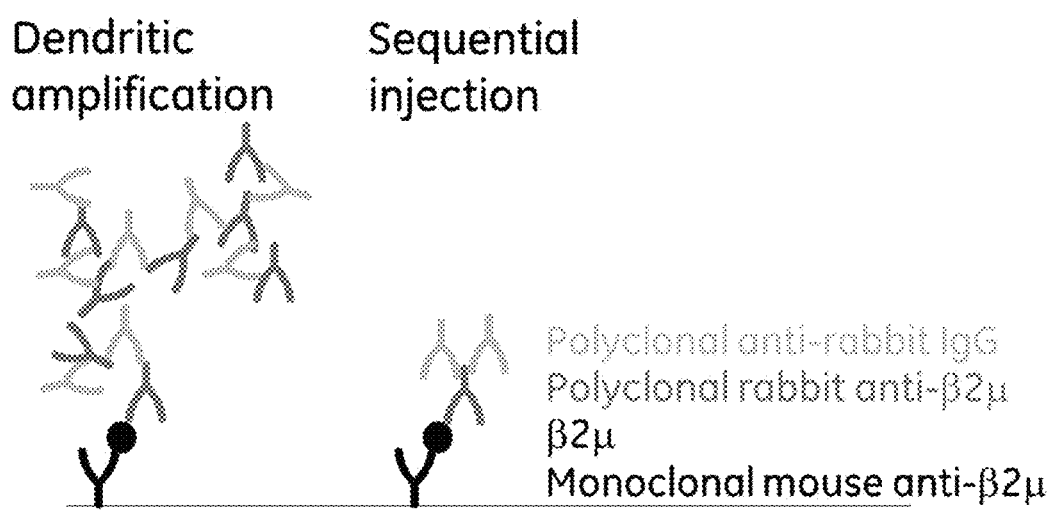
FIG. 1 Schematic drawing comparing simultaneously injection of enhancement molecules (left) and conventional sequential injection (right). In the example beta-2-microglobulin is bound to immobilized monoclonal anti-beta-2-microglobulin and the signal is enhanced with polyclonal rabbit anti-beta-2-microglobulin and anti-rabbit IgG.
Figure 2:
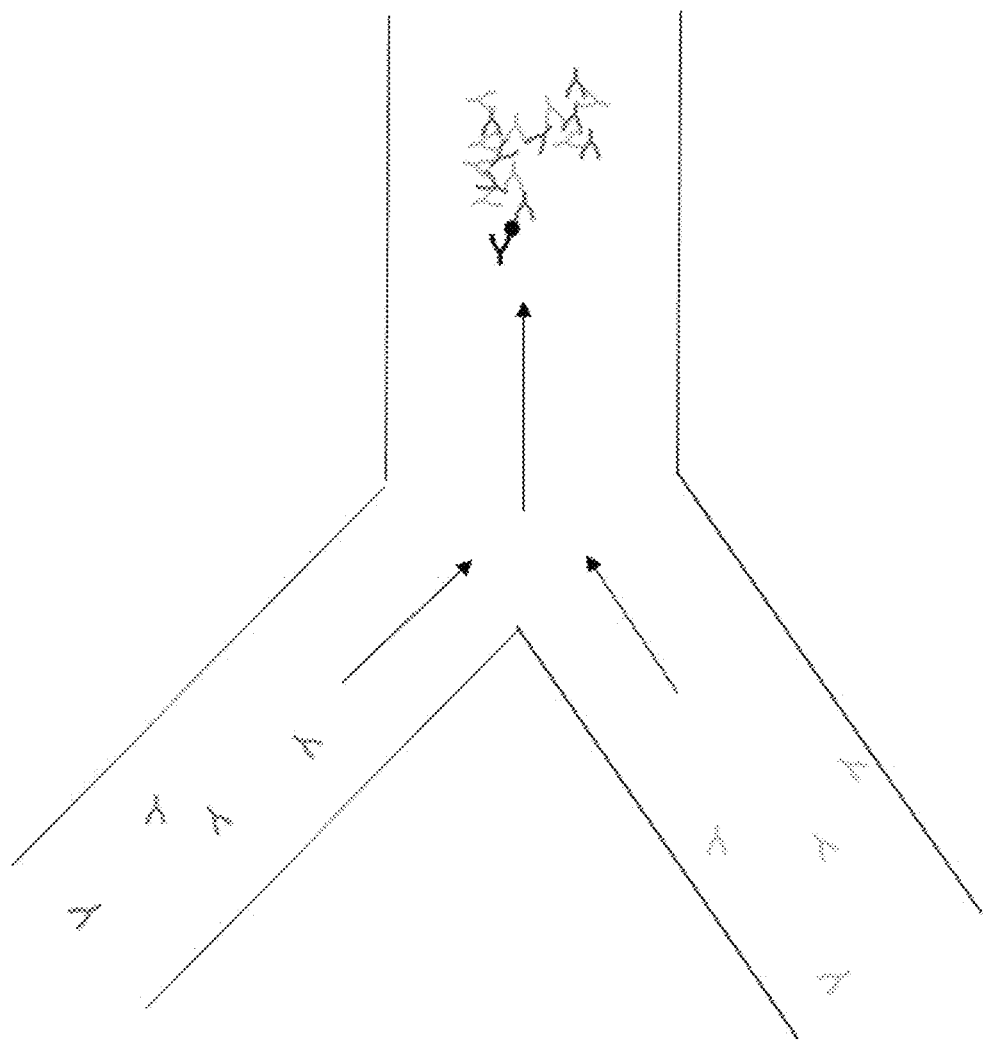
FIG. 2 Schematic drawing illustrating simultaneously injection of enhancement molecules with merged injection for dendritic amplification of the response from an analyte. In this example beta-2-microglobulin is bound to immobilized monoclonal anti-beta-2-microglobulin and the signal is enhanced with polyclonal rabbit anti-beta-2-microglobulin and anti-rabbit IgG.

The invention will now be described more closely in association with the accompanying drawings and the below non limiting examples.

A suitable fluidics system can be composed of a device where two conduits are combined in a junction as described in WO 2008/033073. Here, the two solutions of multivalent molecules are introduced in each conduit so that the two fluids mix at the junction of the flow cell inlet conduit and the mixed fluids pass through the flow cell over the solid support area. The distance between the detection area and the junction, and the fluid flow rates in the first and second conduits should be selected such that when the mixed fluids reach the solid support area, a substantially complete mixing has occurred. Optionally, mixing may be improved by, e.g. directing the fluid mixture into a side channel or loop before redirecting the mixture into the flow cell, or by other means.

There are, of course a number of other ways of obtaining mixing in the micro-fluidic system. These, include, for example, on the one hand, designing the channel system to include stationary constrictions, bends etc which break up the laminar flow or, on the other hand using active mixers. In the latter case a membrane, such as, e.g., the valve membranes present in the microfluidic systems of below mentioned Biacore T200 instrument, may be used as an actuator by vibrating to create stirring which breaks up the laminar flow. Alternatively, one or both fluid flows may be pulsating so that the two solutions are segmented, preferentially into very small segments. Still other alternatives include using alternating valves which micro-segment the flow, micro-propellers, unstable flaps, magnetic stirrers, magnetic beads etc. Instead of active mixers, it would also be possible to use an external field, such as an ultrasound or an electric field, to speed up mixing.

The detection system used for measuring analyte concentration may be based on use of a label or may, preferably, be label-free. Preferably, detection is performed with a sensor, such as a biosensor, in which case the solid support surface is a sensing surface of the biosensor.

A biosensor is broadly defined as a device that uses a component for molecular recognition (for example a layer with immobilised antibodies) in either direct conjunction with a solid state physicochemical transducer, or with a mobile carrier bead/particle being in conjunction with the transducer. While such sensors are typically based on label-free techniques detecting a change in mass, refractive index or thickness for the immobilized layer, there are also biosensors relying on some kind of labelling. Typical sensors for the purposes of the present invention include, but are not limited to, mass detection methods, such as optical methods and piezoelectric or acoustic wave methods, including e.g. surface acoustic wave (SAW) and quartz crystal microbalance (QCM) methods. Representative optical detection methods include those that detect mass surface concentration, such as reflection-optical methods, including both external and internal reflection methods, which may be angle, wavelength, polarization, or phase resolved, for example evanescent wave ellipsometry and evanescent wave spectroscopy (EWS, or Internal Reflection Spectroscopy), both of which may include evanescent field enhancement via surface plasmon resonance (SPR), Brewster angle refractometry, critical angle refractometry, frustrated total reflection (FTR), scattered total internal reflection (STIR) (which may include scatter enhancing labels), optical wave guide sensors, external reflection imaging, evanescent wave-based imaging such as critical angle resolved imaging, Brewster angle resolved imaging, SPR-angle resolved imaging, and the like. Further, photometric and imaging/microscopy methods, "per se" or combined with reflection methods, based on for example surface enhanced Raman spectroscopy (SERS), surface enhanced resonance Raman spectroscopy (SERRS), evanescent wave fluorescence (TIRF) and phosphorescence may be mentioned, as well as waveguide interferometers, waveguide leaking mode spectroscopy, reflective interference spectroscopy (RIfS), transmission interferometry, holographic spectroscopy, and atomic force microscopy (AFR).

Experimental Part

According to the invention, two different enhancement molecules are simultaneously merge injected into a SPR system, such as Biacore T200. Dendritic amplification based on mixing in a fluidics handling device has not been used in combination with SPR detection before. Surprisingly high amplification of the detection signal was achieved with simultaneous injection compared to sequential injection.

The improved sensitivity with dendritic amplification could have significant implications for the detection of a wide range of molecules and biomarkers in complex biological media.

50 μg/ml monoclonal anti-beta-2-microglobulin in 10 mM acetate pH 5.0 was immobilized with standard amine coupling on a CM5 series S sensor chip. The running buffer was 10 mM HEPES, 150 mM NaCl, 3 mM EDTA, 0.05% EDTA pH 7.4.

Dendritic Amplification

Beta-2-microglobulin was injected for 1 min.
50 μg/ml rabbit polyclonal anti-beta-2-microglobulin and 50 μg/ml sheep anti-rabbit IgG was injected simultaneously for 9 min with merged inject.
The surface was regenerated with two 60 s injections with 10 mM glycine pH 1.5.

Sequential Injection

Beta-2-microglobulin was injected for 1 min.
50 μg/ml rabbit polyclonal anti-beta-2-microglobulin was injected for 9 min.
50 μg/ml sheep anti-rabbit IgG was injected for 9 min.

The surface was regenerated with two 60 s injections with 10 mM glycine pH 1.5.

Figure 3:
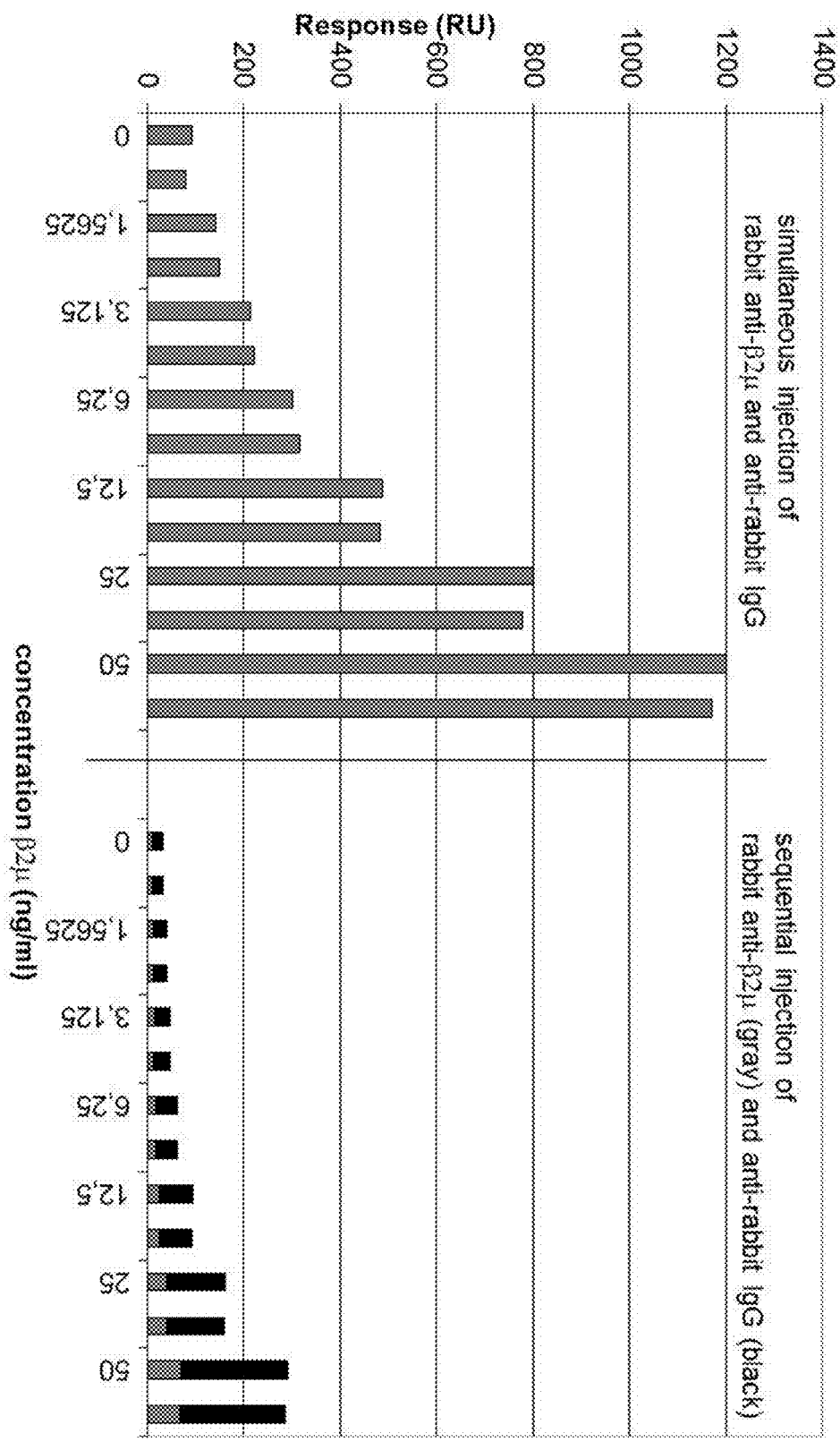
FIG. 3 Comparison of responses between simultaneous injection of enhancement reagents (left) and conventional enhancement with sequential injection (right). For the sequential injections the responses from rabbit anti-β2μ is shown in gray and responses from anti rabbit IgG in black. Samples with 1.56-50 ng/ml β2μ were run in duplicates in randomized order. 50 μg/ml rabbit anti-β2μ and 50 μg/ml sheep anti-rabbit IgG were injected 9 min together or injected 9 min each after each other.

In the example shown in FIG. 3 the enhancement with simultaneous injection of the two enhancement reagent gave at least 15 times higher signal compared to sequential injection of only one enhancement reagent and at least 3 times higher signal compared to sequential injection of the two enhancement reagents (see FIG. 3). For sequential injection the binding of the second enhancement molecules is limited since there is a limited number of binding sites on the first enhancement molecules. The binding level reaches a saturation (see FIG. 4B). For simultaneously injection of the two enhancement reagents no saturation of the enhancement signal is seen under the experimental conditions used in the experiment (see FIG. 4A) since the network of enhancement molecules continue to grow during the injection. The second enhancement reagents binds to the first enhancement reagents and creates more binding sites for the first enhancement reagent. More first enhancement reagents can bind and create more binding sites for the second enhancement reagents and so on.

The results (FIGS. 3-4) showed that dendritic amplification greatly increased the response. 24.5 RU β2μ (stdev 1.2 RU) were enhanced to 1186 RU (stdev 20 RU) with dendritic amplification. Conventional enhancement with polyclonal anti-β2μ gave 70 RU (stdev 0.8 RU). Sequential enhancement with polyclonal anti-β2 followed by anti-rabbit IgG gave additional 220 RU (stdev 2 RU).

In conventional prior art assays, there is usually only one enhancement reagent (see gray bars in the right section of the FIG. 3). Here is also shown the response from the anti-rabbit IgG (black bars) for comparison with the simultaneous injection (left in FIG. 3). As can be seen in FIG. 3 there is a strong amplification of the signal if the enhancement reagents are injected simultaneously with the merge injection compared to sequential injection.

Figure 4A:
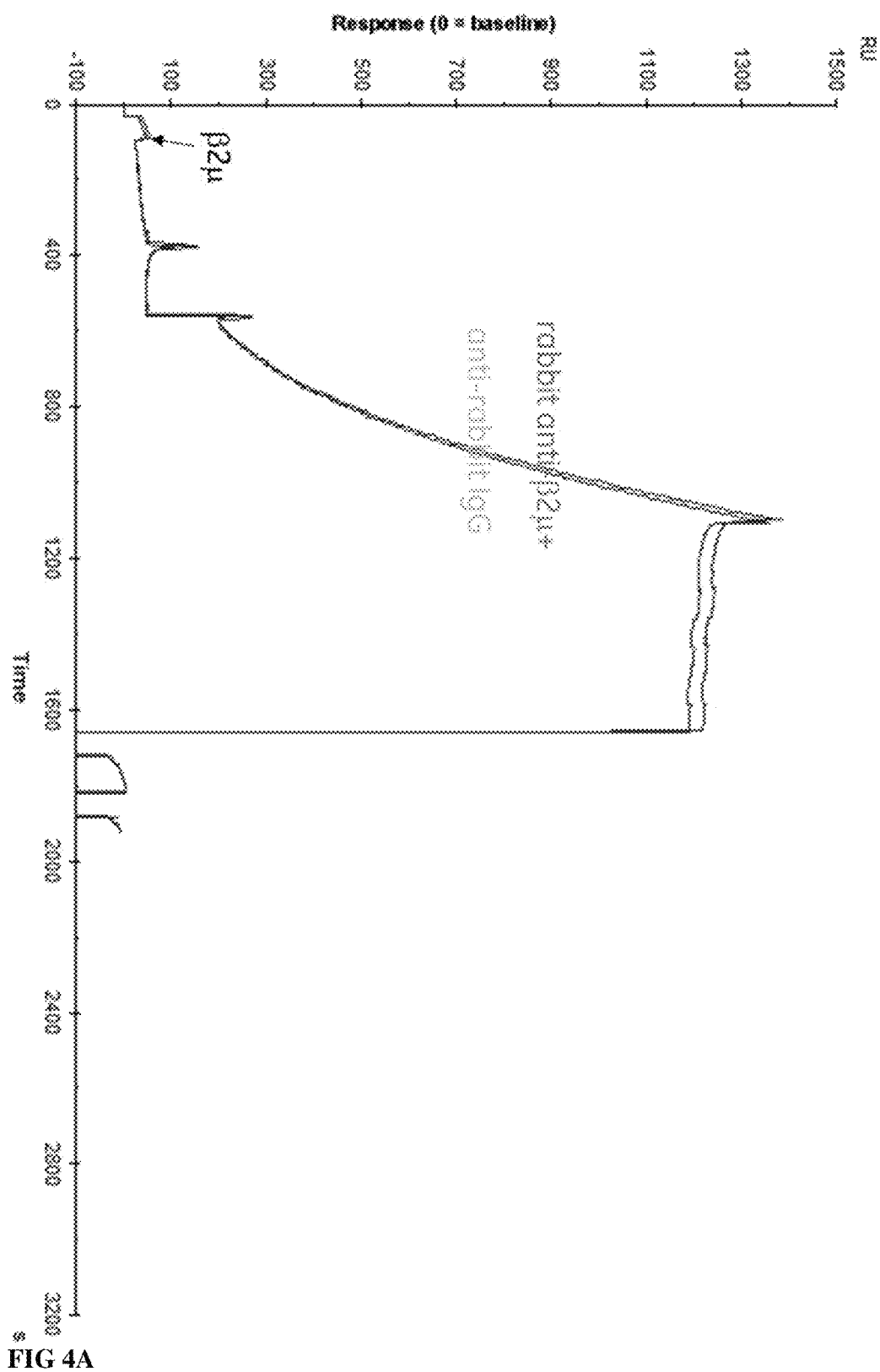
FIG. 4 Sensorgrams showing the different kinetics between the simultaneous injection of enhancement reagents (A) and conventional enhancement with sequential injection (B). The sensorgrams shown are from 50 ng/ml β2μ in flow cell 4. A serial injection was done over flow cell 1-2-3-4 and best result was seen in flow cell 4. The same scale is used in both figures.
Figure 4B:
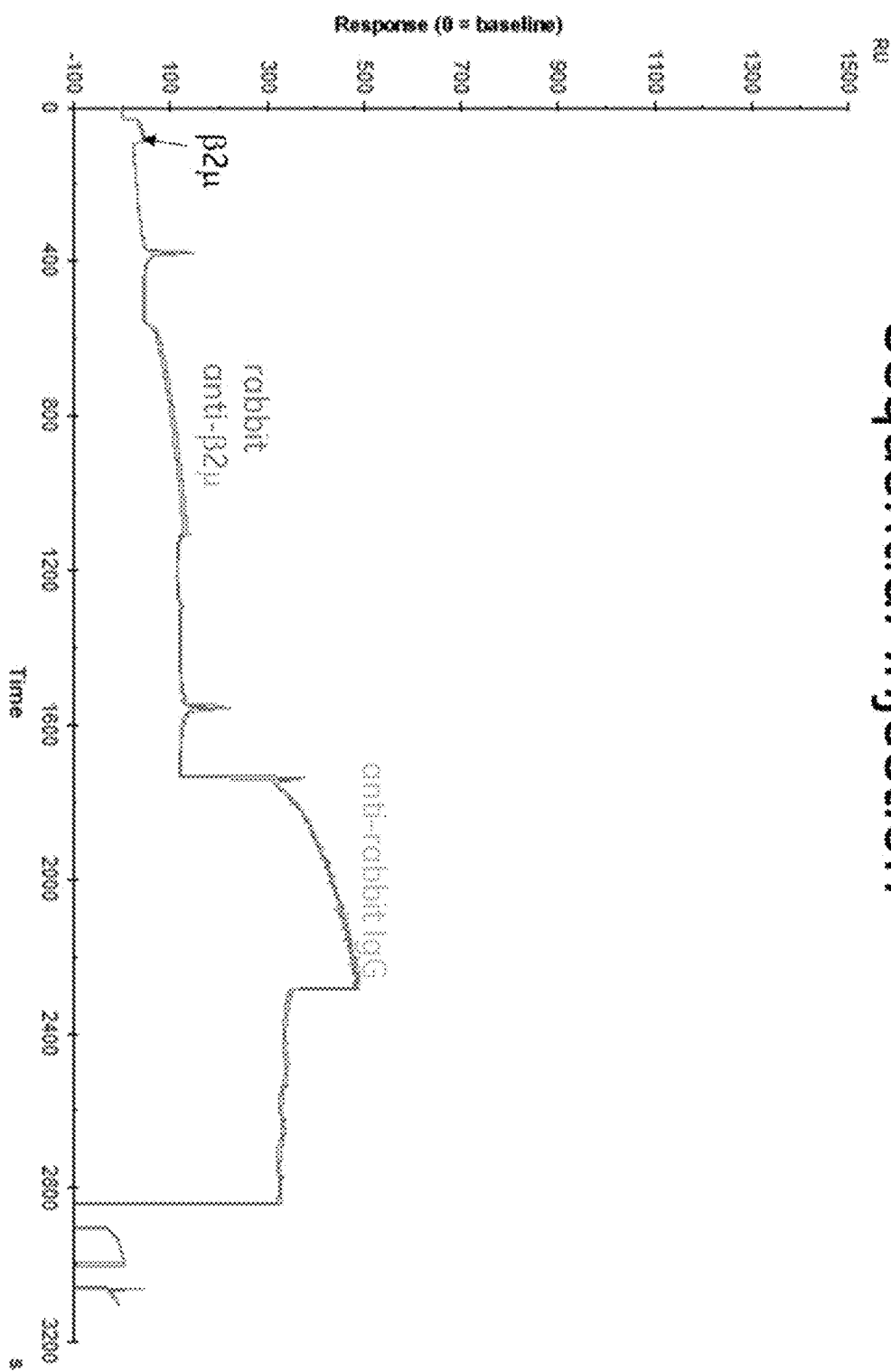

The binding of enhancement reagents increased exponentially when the reagents were injected simultaneously (see sensorgrams in FIG. 4A and compare sequential injection in FIG. 4B). This is due to that a dendritic complex/network is formed. The more the complex grow the more epitopes are available for binding of more enhancement molecules.

If the enhancement reagents instead are injected after each other available binding sites are saturated (see sensorgram in FIG. 4B).

Dendritic amplification has the potential to increase sensitivity in SPR systems, such as Biacore systems T100 (with Immunogenicity Package) and T200 with merged injections. Trace amounts of analyte or enhancement molecules left on the surface after the regeneration can also be amplified so it is important with a good regeneration. The wash of the flow system after injections is also important.

A variant of the purposed method is to inject the analyte together with one of the enhancement solutions (not a separate analyte injection). The analyte could be mixed with the enhancement reagent that do not bind the analyte. In the example above β2μ could have been mixed outside the instrument with anti rabbit IgG. β2μ+anti-rabbit IgG could then be injected from one channel and anti β2μ from the other channel.

Another variant of the purposed method is possible if the analyte has multiple binding sites for the enhancement molecule and the enhancement molecule has multiple binding sites for the analyte. The analyte and enhancement should then be injected simultaneous but separately. In this case a second enhancement reagent is not needed.

REFERENCES

Power-free microchip immunoassay of PSA in human serum for point-of-care testing. Okada H, Hosokawa K, Maeda M. Anal Sci. 2011; 27(3):237-41.
Immunoassay on a power-free microchip with laminar flow-assisted dendritic amplification. Hosokawa K, Omata M, Maeda M. Anal Chem. 2007 Aug. 1; 79(15):6000-4.
Spatial distribution of laminar flow-assisted dendritic amplification. Hosokawa and Maeda, Lab on Chip 2009, 9, 464-468.
Enhanced surface plasmon resonance immunosensing using a streptavidin-biotinylated protein complex. Pei R, Yang X, Wang E. Analyst. 2001 January; 126(1):4-6.
Supramolecular formation of antibodies with viologen dimers: utilization for amplification of methyl viologen detection signals in surface plasmon resonance sensor. Yamaguchi H, Harada A. Biomacromolecules. 2002 November-December; 3(6):1163-9.

The invention claimed is:

1. A method for detecting with a biosensor a binding event between a binding agent on a solid support and an analyte, comprising:
   simultaneously and separately adding a first enhancement reagent having affinity for said analyte and a second enhancement reagent having affinity for said first enhancement reagent, wherein the first enhancement reagent binds to the analyte and the second affinity agent binds to the first enhancement reagent, and wherein the first and second enhancement reagents have more than one binding site so that they are also able to bind to each other to thereby amplify a detectable signal generated by the binding event; and
   detecting, using a label-free detection technique, the detectable signal with the biosensor.

2. The method of claim 1, wherein the first and second enhancement reagents are simultaneously injected to the solid support via a flow channel system.

3. The method of claim 2, wherein the first and second enhancement reagents have undergone a substantially complete mixing before entering a detection area of a biosensor surface.

4. The method of claim 1, comprising addition of the analyte before addition of the enhancement reagents.

5. The method of claim 1, comprising addition of the analyte together with the second enhancement reagent.

6. The method of claim 1, wherein the binding agent is a monoclonal antibody directed against the analyte; the first enhancement reagent is a polyclonal antibody with binding sites for the analyte and the second enhancement reagent; and the second enhancement reagent is a polyclonal antibody directed against the first enhancement reagent.

7. The method of claim 1, wherein the analyte is present in a concentration of 1.56 nm/ml to 50 ng/ml.

8. The method of claim 1, wherein the label-free detection technique comprises evanescent wave sensing.

9. The method of claim 1, wherein the detection is performed in a flow cell.

10. The method of claim 9, wherein the flow cell comprises a detection area with the binding agent, and an inlet which via a junction is connected to first and second conduits, wherein the binding agent is an immobilized ligand, and wherein the first and second enhancement reagents mixing comprises flowing the reagent solutions in respective conduits so that the two fluids mix at the junction of the flow cell inlet conduit and the mixed fluids pass through the flow cell over the detection area.

11. The method of claim 10, wherein the mixed fluids reach the detection area when a substantially complete mixing has occurred.

12. The method of claim 1, wherein the label-free detection technique comprises surface plasmon resonance (SPR).

* * * * *